(12) United States Patent
Egnelöv et al.

(10) Patent No.: US 8,118,831 B2
(45) Date of Patent: Feb. 21, 2012

(54) CLOSURE DEVICE AND METHOD FOR SEALING A PUNCTURE IN A BLOOD VESSEL

(75) Inventors: Per Egnelöv, Uppsala (SE); Fredrik Preinitz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 1079 days.

(21) Appl. No.: 10/756,764

(22) Filed: Jan. 14, 2004

(65) Prior Publication Data

US 2004/0204741 A1    Oct. 14, 2004

Related U.S. Application Data

(60) Provisional application No. 60/439,800, filed on Jan. 14, 2003.

(51) Int. Cl.
*A61B 17/08*    (2006.01)
*A61D 1/00*    (2006.01)

(52) U.S. Cl. ........................................... 606/213

(58) Field of Classification Search .................. 606/103, 606/72, 228–232, 108, 139–150, 213–217; 623/23.72
See application file for complete search history.

(56) References Cited

U.S. PATENT DOCUMENTS

| | | | |
|---|---|---|---|
| 3,760,627 A | | 9/1973 | Richardson et al. |
| 4,796,612 A | | 1/1989 | Reese |
| 5,021,059 A | * | 6/1991 | Kensey et al. ............... 606/213 |
| 5,098,433 A | | 3/1992 | Freedland |
| RE34,021 E | * | 8/1992 | Mueller et al. ............... 604/533 |
| 5,250,049 A | | 10/1993 | Michael |
| 5,342,393 A | * | 8/1994 | Stack ........................... 606/213 |
| 5,350,399 A | | 9/1994 | Erlebacher et al. |
| RE34,866 E | * | 2/1995 | Kensey et al. ............... 606/213 |
| 5,411,520 A | * | 5/1995 | Nash et al. .................... 606/213 |
| 5,433,053 A | | 7/1995 | Tulloch |
| 5,531,759 A | | 7/1996 | Kensey et al. |
| 5,545,178 A | * | 8/1996 | Kensey et al. ............... 606/213 |
| 5,593,422 A | | 1/1997 | Muijs van de Moer et al. |
| 5,662,681 A | * | 9/1997 | Nash et al. .................... 606/213 |
| 5,666,710 A | | 9/1997 | Weber et al. |
| 5,681,334 A | * | 10/1997 | Evans et al. .................. 606/148 |
| 5,800,436 A | | 9/1998 | Lerch |
| 5,861,003 A | | 1/1999 | Latson et al. |

(Continued)

FOREIGN PATENT DOCUMENTS

EP    1 266 626 A1    12/2002

(Continued)

OTHER PUBLICATIONS

U.S. Appl. No. 10/018,137, filed Mar. 20, 2002, Akerfeldt et al.

*Primary Examiner* — Melanie Tyson
(74) *Attorney, Agent, or Firm* — Foley & Lardner LLP (57) ABSTRACT

A closure device for sealing a percutaneous puncture in the wall of a blood vessel includes: an insertion tool having an actuator which is operable in a first mode in which the actuator is configured for deployment of an inner seal inside the vessel and operable in a second mode in which the actuator is configured for tamping a locking member on an outside of the vessel, where the actuator is arranged to be set into the second mode in response to a pulling force acting on a filament connecting the inner seal and the locking member.

30 Claims, 6 Drawing Sheets

U.S. PATENT DOCUMENTS

| | | |
|---|---|---|
| 5,928,264 A | 7/1999 | Sugarbaker et al. |
| 6,024,756 A | 2/2000 | Huebsch et al. |
| 6,045,551 A * | 4/2000 | Bonutti .......................... 606/60 |
| 6,270,500 B1 | 8/2001 | Lerch |
| 6,325,789 B1 | 12/2001 | Janzen et al. |
| 6,379,363 B1 | 4/2002 | Herrington et al. |
| 6,425,911 B1 * | 7/2002 | Akerfeldt et al. ............. 606/213 |
| 6,491,714 B1 | 12/2002 | Bennett |
| 6,508,828 B1 | 1/2003 | Akerfeldt et al. |
| 6,929,655 B2 * | 8/2005 | Egnelov et al. ................ 606/213 |
| 2001/0003158 A1 * | 6/2001 | Kensey et al. ................ 606/213 |

FOREIGN PATENT DOCUMENTS

| | | |
|---|---|---|
| WO | WO 00/78226 A1 | 12/2000 |

* cited by examiner

CLOSURE DEVICE AND METHOD FOR SEALING A PUNCTURE IN A BLOOD VESSEL

CROSS-REFERENCE TO RELATED PATENT APPLICATIONS

The present application claims priority to U.S. Provisional Application No. 60/439,800, filed on Jan. 14, 2003, the contents of which are hereby incorporated by reference.

FIELD OF THE INVENTION

The present invention relates generally to a closure device for sealing a percutaneous puncture in the wall of a blood vessel, and more particularly to a closure device and a method by which an inner seal is deployed inside a vessel and a locking member is secured outside the vessel, such that bleeding from the percutaneous puncture is prevented.

BACKGROUND OF THE INVENTION

A system for sealing a percutaneous puncture in a blood vessel can comprise an inner seal which is adapted to be positioned against an inner surface of the vessel wall, and a locking member which is connected to the inner seal by, for example, a filament or a suture, and which is adapted to be positioned against an outer surface of the vessel wall such that the percutaneous puncture is sealed there between. During the phase of insertion, the inner seal is folded inside an introducer tube which is resting in the puncture to provide access to the interior of the blood vessel. Deployment of the inner seal inside the vessel takes place by pushing the inner seal through the tube, out from the distal end opening of the introducer. To ensure proper unfolding of the inner seal, the inner seal has to be deployed some distance away from the puncture hole in the vessel wall before the inner seal is positioned to be securely seated against the inner surface of the vessel wall. When the inner seal has been deployed inside the blood vessel, the introducer is retracted from the puncture to rest with its distal end outside the vessel, in close proximity to the puncture. When, during said retraction, the inner seal has been positioned against the vessel wall to cover the puncture, the locking member is pushed forward through the introducer tube until the locking member is tamped in contact with the outer surface of the vessel wall. To effectuate the different actions described above, inserter tools have been proposed which also accommodate the inner seal and the locking member before the sealing procedure.

The devices and procedures for sealing a percutaneous puncture in a blood vessel may be improved with respect to drawbacks connected with the prior art systems:

For example, existing systems unconditionally allow tamping of the locking member and provide no verification that the distal end of the introducer is retracted from the puncture before tamping, leading to a possibility of the locking member unintentionally being positioned inside the vessel in case of an incorrect maneuver.

Another drawback in existing systems is that two hands typically are required to handle existing tools for deployment of the inner seal, seating the inner seal against the vessel wall, and for tamping of the locking member.

SUMMARY OF THE INVENTION

The present invention aims to solve at least one of these and other problems.

An object of the present invention is to provide a closure device and method by which proper closure and ease of handling are both enhanced upon sealing of a percutaneous puncture in the wall of a blood vessel after a medical treatment or surgery.

In one aspect, the present invention aims to provide a closure device by which is eliminated the possibility of the locking member being unintentionally positioned inside the blood vessel.

In another aspect, the present invention aims to provide a closure device by which it is ensured that the inner seal is seated against the vessel wall before tamping of the locking member.

In a further aspect, the present invention aims to provide a closure device and method by which: deployment of an inner seal inside the vessel; seating the inner seal against the inner side of the vessel wall; and tamping of a locking member such that bleeding through the puncture is prevented, may all be performed in a one-hand operation.

Briefly, the present invention provides a closure device for sealing a percutaneous puncture in the wall of a blood vessel, comprising an insertion tool having an actuator which is operable in a first mode for deployment of an inner seal inside the vessel and operable in a second mode for tamping of a locking member outside the vessel, the actuator being arranged to be set into said second operable mode in response to a pulling force acting on a filament connecting the inner seal and the locking member.

Preferably, the actuator is controlled by an actuator mechanism that is adapted to disable the actuator until a pulling force acting on the filament causes the actuator to be reset into said second operable mode.

According to another preferred embodiment of the present invention, a method for sealing a percutaneous puncture in the wall of a blood vessel may comprise: providing an insertion tool having an actuator which is operable in a first mode for deployment of an inner seal inside the vessel and operable in a second mode for tamping a locking member on an outside of the vessel, the actuator being arranged to be set into the second mode in response to a pulling force acting on a filament connecting the inner seal and the locking member; operating the insertion tool in the first mode; pulling the filament so as to set the actuator in the second mode; and operating the insertion tool in the second mode.

BRIEF DESCRIPTION OF THE DRAWINGS

The invention is more closely described below by reference to the drawings, diagrammatically illustrating the new insertion tool and method. In the drawings.

FIG. 13a is a partially broken away elevation view of a slider, incorporated in the closure device;

FIG. 13b is a top view of the slider of FIG. 13a;

DETAILED DESCRIPTION OF PREFERRED EMBODIMENTS

A closure device for sealing a percutaneous puncture in a blood vessel is generally referred to by reference numeral 1 in the drawings. In FIGS. 4-10, the closure device 1 is diagrammatically shown in different operative positions illustrating the procedural steps of the sealing operation. In FIGS. 11-15, the structure and operation of an actuator mechanism in the closure device 1 is illustrated and explained, by way of example.

Figure 1:
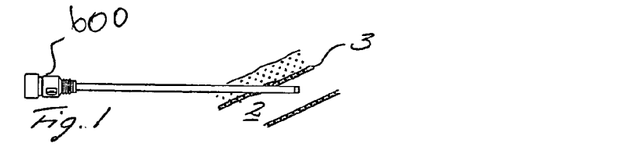
FIG. 1 illustrates a blood vessel in which a distal end of an introducer is positioned.

FIG. 1 illustrates an introducer 600 whose distal end portion is introduced into a blood vessel 2 and whose proximal portion extends out from the skin of a patient. Presumably, a medical operation has been performed via the introducer 600, and the puncture hole through the wall 3 of the blood vessel is now to be closed.

Figure 2:
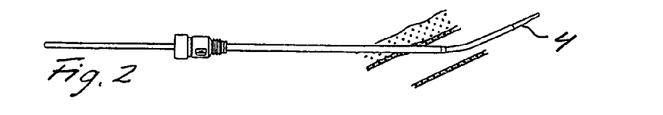
FIG. 2 illustrates a guide rod being inserted through the introducer of FIG. 1.

In order to replace the introducer 600 with a closure device 1 according to the present invention, a guide rod 4 may be inserted through the introducer 600 as is shown in FIG. 2.

Figure 3:
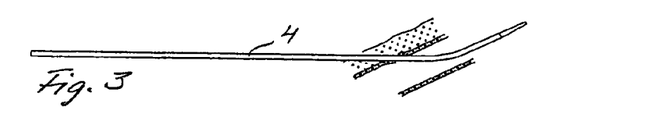
FIG. 3 illustrates the vessel in which only the guide rod is in place.

In FIG. 3 the introducer 600 has been removed, leaving only the guide rod 4 in place. An advantage achieved by the use of a guide rod is that the diameter of the guide rod is larger than the diameter of a guide wire, e.g., which in the case of an artery results in less blood flowing from the artery, and the necessity for a manual external compression may thereby be avoided.

Figure 4:
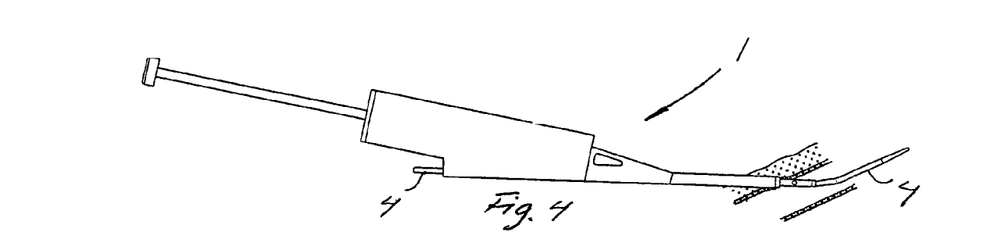
FIG. 4 illustrates a closure device according to the present invention, the closure device being positioned over the guide rod of FIG. 3.

FIG. 4 shows a closure device 1 according to the present invention, threaded over the guide rod 4. This is in contrast to insertion tools that are adapted to be connected to an existing introducer 600. The present closure device 1 is therefore independent of the type, e.g., diameter or length, of the introducer 600 that was previously inserted into the vessel.

Figure 5:
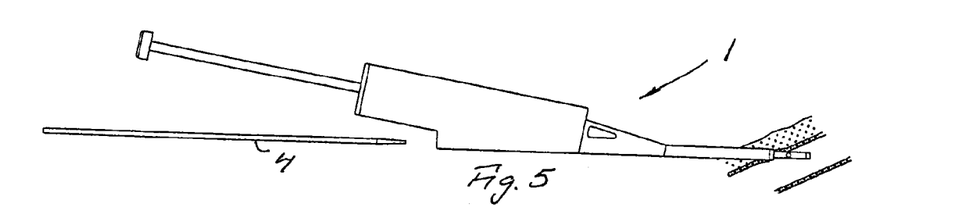
FIG. 5 illustrates how the guide rod is removed from the closure device and from the vessel.
Figure 6:
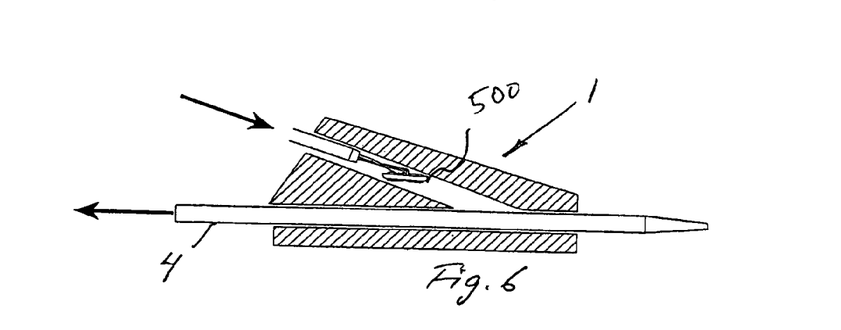
FIG. 6 is a diagrammatic, cross-sectional view of internal passageways that guide the seal assembly and the guide rod, respectively, in a housing of the closure device.

When the correct positioning of the closure device 1 has been established, the guide rod 4 is removed as is illustrated in FIGS. 5 and 6.

FIG. 6 shows, diagrammatically, a cross-section of a forward portion of the housing 100 of the closure device 1. From the drawing it can be seen that a first passageway, in which seal assembly 500 is positioned, connects to a second passageway in which the guide rod 4 moves. Here it should be noted that it is possible to let the first and second passageways switch places, such that the guide rod 400, which is flexible, is inserted through the first passageway. It is also conceivable to have two passageways that both are slightly bent. Two passageways can also connect to a straight passageway, which gives a configuration having the shape of the letter Y.

Figure 7:
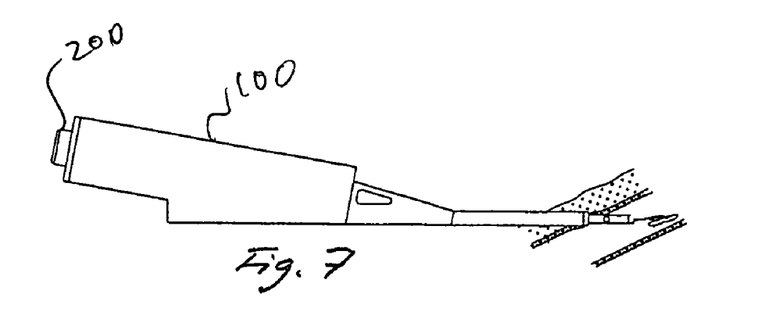
FIG. 7 illustrates how an actuator is pushed into the housing for deployment of an inner seal in a first mode of operation.

As illustrated in FIG. 7, an actuator 200 is depressed into the proximal end of the closure device housing 100. When the distal end of the device 1 is positioned in the blood vessel, the guide rod 4 is removed, and the operator pushes the actuator 200 towards an end position provided in the housing 100. The actuator 200 is operatively associated, in a first relative position, with a sliding member 300 that carries a tamping tube 505 and a pusher 506, the latter detachably carrying an inner seal 501 by its distal end and pushing the inner seal 501 out from the closure device 1 to be deployed inside the vessel. This step completes a first mode of operation of the actuator mechanism.

One embodiment of the actuator mechanism, which is accommodated in the housing 100 of the closure device 1, is diagrammatically illustrated and further explained below with reference to FIGS. 11-15. An important feature of the mechanism is that the locking member 502, which is carried behind the inner seal 501 on a filament 503, cannot be pushed out from the closure device 1 unintentionally when the actuator 200 has been pushed into its end position. An erroneous tamping of the locking member 502 inside the vessel is thereby prevented. The mechanism 200 comprises a spring member 207 generating a biasing force acting on the actuator as the actuator is pushed into the housing 100. When the actuator 200 reaches its end position, a snap lock connection temporarily arrests the actuator in this end position.

Figure 8:
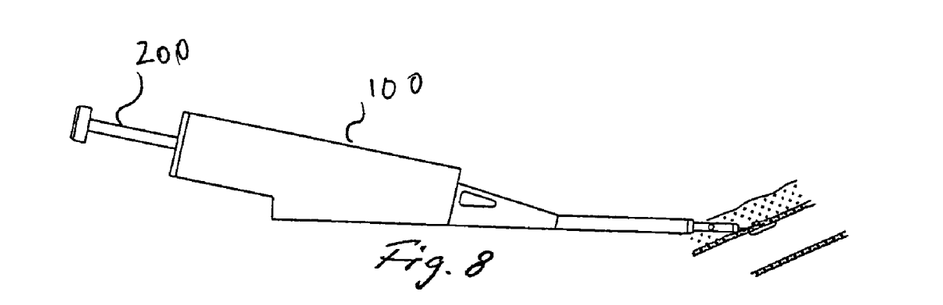
FIG. 8 illustrates how the closure device is retracted until the inner seal is in contact with the vessel wall.

Referring now to FIG. 8, in the next step of the sealing operation the housing 100 is manually retracted, i.e., the housing 100 is pulled in the proximal direction until the inner seal 501 is seated over the puncture in contact with the inner surface of the vessel wall 3, while simultaneously the distal end of the closure device 1 is retracted from the puncture.

During retraction of the closure device 1, the pulling force is carried by the filament 503 which is arrested by its distal end being attached to the inner seal 501 and by its proximal end being connected to the sliding member 300. The filament 503 thus prevents the sliding member 300 from moving in the proximal direction, causing the sliding member 300 to be displaced relative to the actuator 200. By means of a cam surface provided on the sliding member 300, the snap connection that arrests the actuator 200 is disengaged in response to the relative displacement between the retracting actuator 200 and the stationary sliding member 300. As the snap connection is disengaged, the biasing spring 207 pushes the actuator 200 back to a tamping position wherein the actuator 200 is again operatively associated with the sliding member 300, now in a second relative position. Furthermore, during this retraction of the housing 100, the proximal end of the pusher is disconnected from engagement with the sliding member 300, and a subsequent second forward motion of the actuator 200 will have no effect on the pusher 506. In the tamping operation the actuator 200 acts on the sliding member 300, the tamping tube 505 and the locking member.

Figure 9:
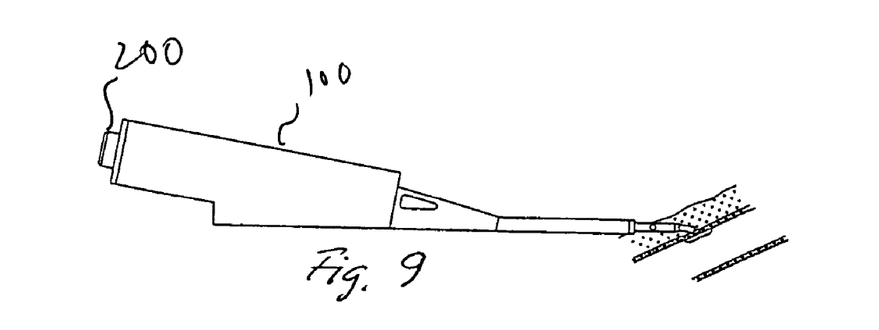
FIG. 9 illustrates how the actuator is pushed into the housing for tamping of a locking member in a second mode of operation.

FIG. 9 illustrates the actions caused by a second forward motion of the actuator 200. When the actuator 200 this second time is pushed towards its end position in the housing 100, the actuator 200 pushes on the sliding member 300 which, via the tamping tube 505, pushes the locking member forward and into a locking position against the outer surface of the vessel wall 3, as is illustrated in FIG. 9. This step completes the second mode of operation of the actuator mechanism.

The filament 503 runs through the locking member 502. In the tamped position, the filament 503 secures the locking member 502 by means of frictional engagement provided from a distal portion of the filament 503, the portion having an enlarged dimension or diameter.

The proximal end of the filament 503 is attached to the sliding member 300 through a sliding connection. In the first mode, when the actuator 200 and sliding member 300 are pushed forward for deployment of the inner seal 501, the filament 503 is tensioned by the pusher 506 gripping the inner seal 501 by its distal end. In the second mode, as the actuator 200 and sliding member 300 are pushed forward for tamping the locking member 502, the pusher 506 is inactive and the filament 503 is arrested by a member which is stationary relative to the sliding member 300 and which maintains a tension of the filament 503. At the very end of the forward motion, the proximal end of the filament 503 is released from the sliding member 300 by the action of the stationary member.

Here it should be noted that one person can perform the closure using one hand only throughout the whole sealing procedure.

Figure 10:
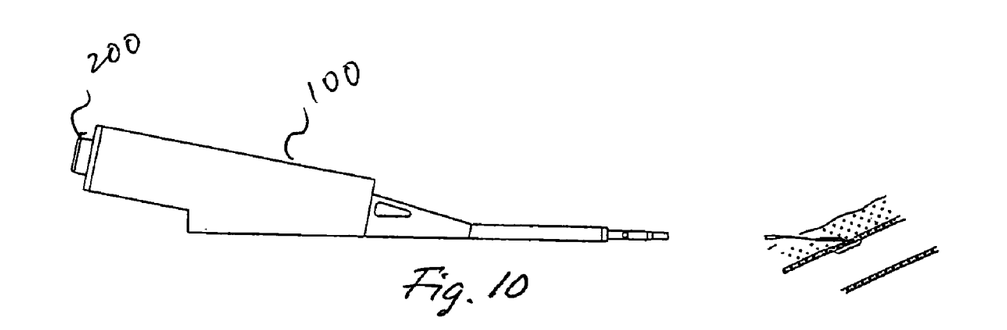
FIG. 10 illustrates the closure device after completion of the sealing operation.

The housing 100 and its associated components can now be removed and disposed of, thereby leaving only the inner seal 501, the locking member 502 and the filament 503 in place, as is illustrated in FIG. 10. Cutting the filament 503 completes the sealing operation.

As will be more fully understood from the following description of the device, the present invention discloses a method for sealing a percutaneous puncture in the wall of a blood vessel, comprising the step of providing an insertion tool having an actuator 200 which is operable in a first mode for deployment of an inner seal 501 inside the vessel 2 and operable in a second mode for tamping of a locking member 502 on the outside of the vessel 2, wherein operation of the actuator 200 for tamping the locking member 502 is enabled through the step of applying a pulling force to act on a filament 503, connecting the inner seal 501 and the locking member 502, for setting the actuator 200 into the second operable mode.

Preferably, the step of operating the actuator 200 for deployment of the inner seal 501 disables operation of the actuator 200 for tamping the locking member 502, until the step of applying a pulling force to act on the filament 503 resets the actuator 200 into the second operable mode.

In the present description of an illustrated embodiment, "distal" refers to the left hand side and "proximal" refers to the right hand side of the drawings of FIGS. 11-15. Also, the expressions "top", "bottom", "horizontal" and "vertical" refer entirely to the orientation shown in the drawings, and is no indication of the actual orientation of the closure device in practice.

Figure 11:
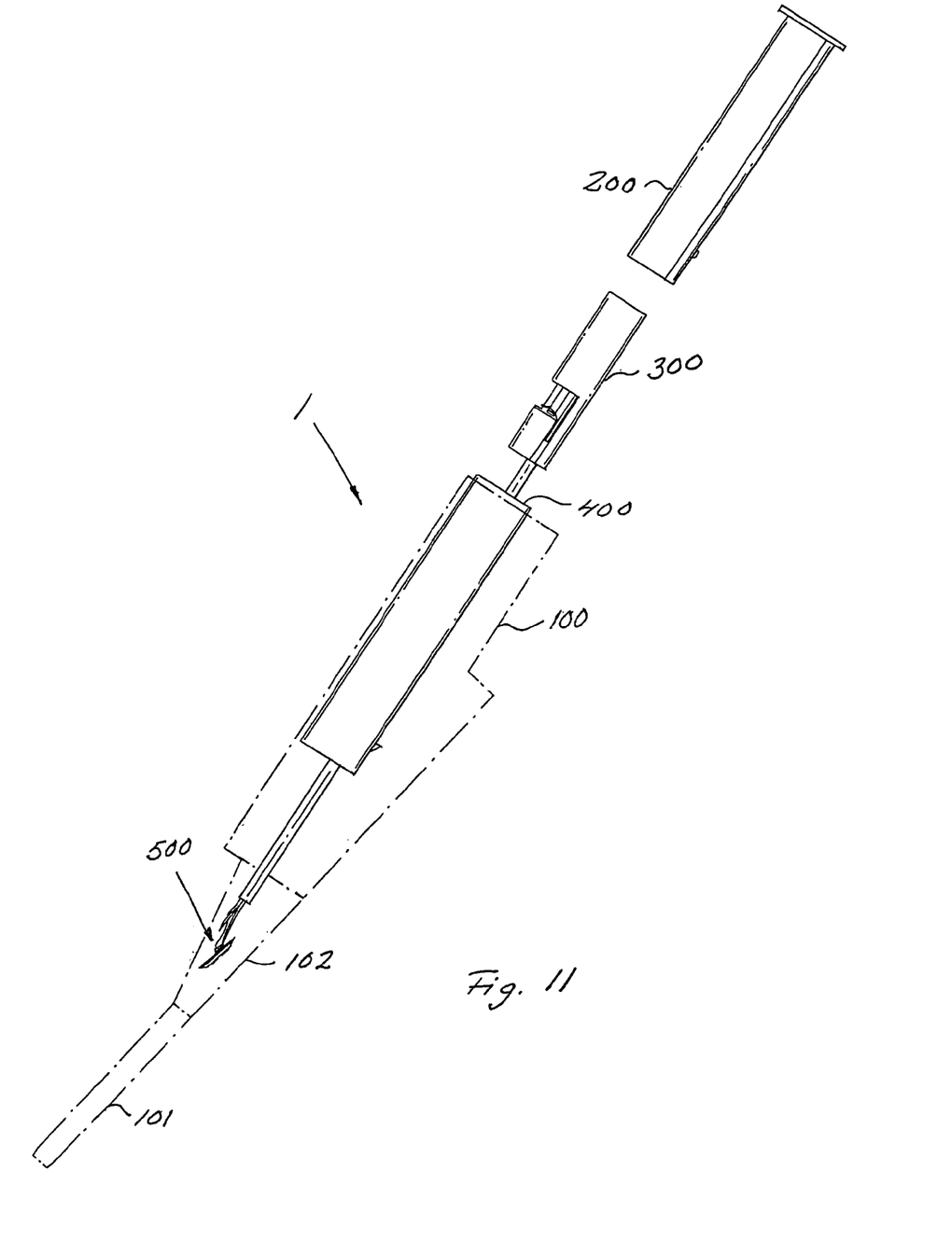
FIG. 11 is an exploded view showing the major components of one embodiment of the closure device according to the present invention.

With reference to FIG. 11, the closure device 1 comprises as its major components: a housing 100 (outlined in dash-dot lines), and an actuator 200, a slider 300, a sleeve 400 and a seal assembly 500, all supported in the housing 100.

Basically, the sleeve 400 is telescopically received in the housing 100, the actuator 200 is telescopically received in the sleeve 400, the seal assembly 500 is operatively connected to the slider 300, and the slider 300 is operatively engaged by the actuator 200. The slider 300 is guided for longitudinal displacement relative to the actuator 200 between first and second relative positions, in which the actuator 200 operatively engages the slider 300 to be brought into the movement of the actuator 200. The actuator 200 is guided for longitudinal movement relative to the sleeve 400, from an extended storage or idle position to a partially overlapping operable position from where the actuator 200 is further advanced to an end position for deployment of the inner seal 501 in the first mode, and for tamping the locking member 502 in the second mode of operation. The sleeve 400 is accommodated in the housing 100 and guided therein for longitudinal movement, from an extended idle position to a fully inserted operative position. Advantageously, the housing 100, sleeve 400 and actuator 200 are arranged about a common longitudinal axis. The housing, the sleeve and the actuator, as well as the slider, may be of any suitable sectional profile, such as circular, or they may for example have an orthogonal section such as the illustrated embodiment of a closure device 1 according to the invention. As an assembly, these components provide a tool for insertion of the sealing components such as the inner seal 501, the filament 503 and the locking member 502.

The housing 100 is associated with an insertion tube 101, connecting to the distal end of the housing via a forward house portion 102 (as seen in the direction of insertion). Insertion tube 101 and house portion 102 may be integral parts of the housing 100. When inserted by its distal end through the puncture, the insertion tube 101 communicates the blood vessel with first and second passageways formed in the forward house portion 102 (as shown in FIG. 6), one of which is designed to receive a guide rod 4 that controls the insertion tube 101 during location in the blood vessel, and the other passageway designed for insertion of the inner seal 501 and locking member 502 upon sealing of the puncture. These passageways converge into the insertion tube 101. Advantageously, the housing 100 is formed with indication means providing a verification that a flow communication has been established with the blood vessel, via the distal end of housing 100/insertion tube 101. Such a means will be known to one of ordinary skill in the art.

Figure 12:
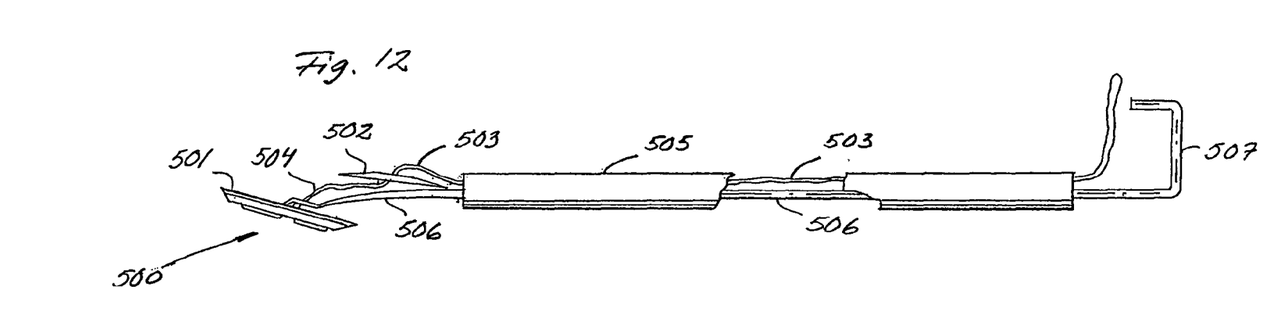
FIG. 12 is a partially broken away elevation view of a seal assembly and associated elements of the closure device.

With reference to FIG. 12, the seal assembly 500 comprises the inner seal 501 and the locking member 502, the inner seal 501 being anchored in the distal end of the suture or filament 503 running through the locking member 502. The locking member 502 is spaced behind the inner seal 501, on the proximal side of an end portion 504 of the filament 503 having increased cross-sectional dimension, providing a frictional engagement with the locking member 502 in its tamped (advanced) position on the filament 503. In a ready-to-use condition, the inner seal 501 and locking member 502 both lie encapsulated in the forward house portion 102 (diagrammatically illustrated in FIG. 11).

The filament 503 runs through the tamping tube 505, together with the pusher 506. The filament 503 and the pusher 506 both reach out beyond the distal end of the tamping tube 505, the pusher 506 by its distal end detachably gripping the inner seal 501, and the locking member 502 freely supported on the filament 503 outside the distal end of the tamping tube 505. Also, the filament and the pusher both reach out from the proximal end of the tamping tube 505. The proximal ends of the filament 503, the pusher 506 and the tamping tube 505 are all supported in the slider 300, as will be explained below with reference also to FIGS. 13a-13d.

Figures 13A, 13B:
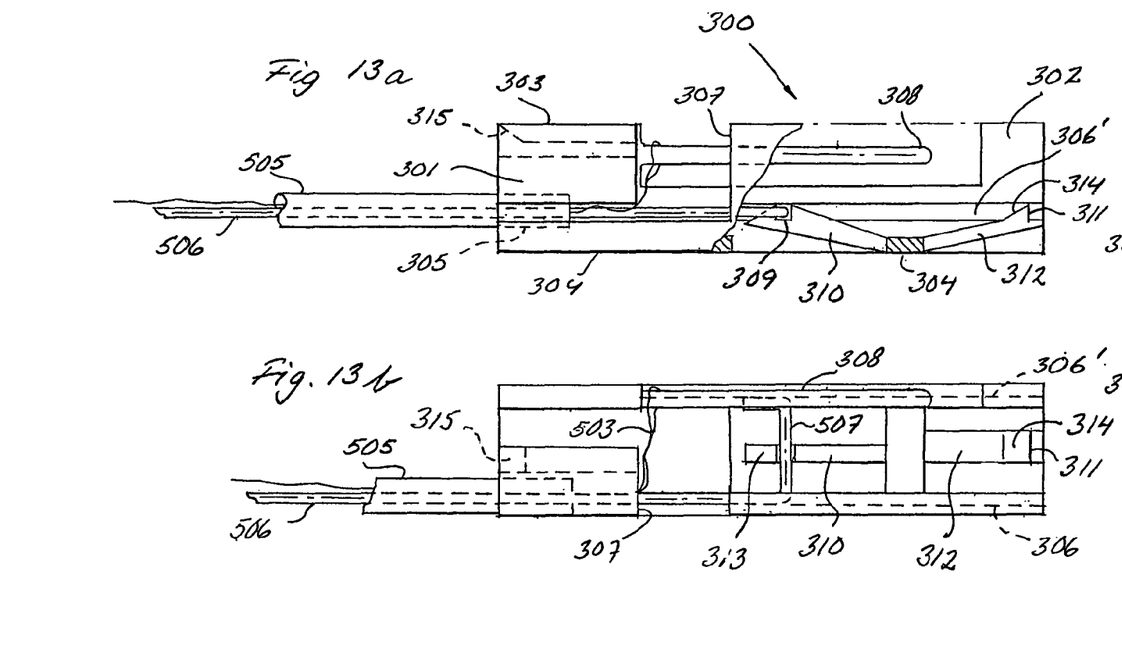
Figures 13C, 13D:
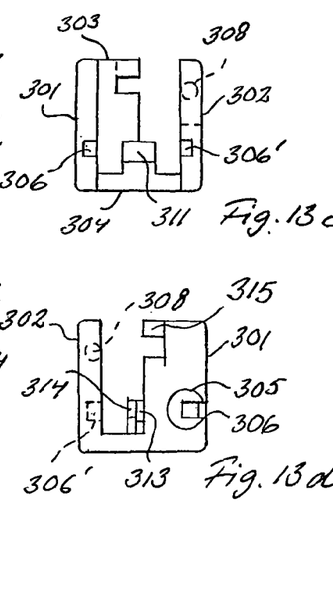
FIG. 13c shows the proximal end of the slider.
FIG. 13d shows the distal end of the slider.

Referring now to FIGS. 13a and 13b, the slider 300 is an elongate four-sided body having an orthogonal section, dimensioned to be accommodated in the actuator 200 for longitudinal movement therewith, and guided in the actuator 200 for longitudinal displacement relative thereto. In FIGS. 13c-13d, the slider 300 has opposed, vertical side walls 301, 302 connecting a horizontal top plane 303 with a horizontal bottom plane 304. Preferably, the longitudinal margins connecting the walls are chamfered in order to facilitate a sliding displacement free from jamming in the actuator 200.

The tamping tube 505 connects to the distal end of the slider 300, the proximal end of the tamping tube 505 being received in a recess 305, mouthing in the distal end of the slider 300.

In one side wall 301 of the slider 300, the recess 305 opens laterally towards the exterior, the opening forming a slot 306 that connects the recess 305 with a clearance 307 through the side wall 301. On the interior of side wall 301, the slot 306 proceeds rectilinearly from the clearance 307 to the proximal end of slider 300. A corresponding slot 306' is formed on the interior of the opposite side wall 302. The slots 306, 306' are dimensioned to receive and to guide the pusher 506, the proximal end 507 of the pusher being bent transversely to reach across the interior of slider 300 for a sliding engagement with the two slots 306, 306'.

The filament 503 is detachably connected to the slider 300 through a sliding connection. The proximal end of the filament 503 is arrested in the slider 300 by being looped around a longitudinal bar 308, cut out from the opposite side wall 302. The bar 308 extends from a distal portion of the slider 300, and terminates with a free end in a proximal portion of the slider 300. The filament 503 runs, under a slight tension, from the bar 308 across the interior of slider 300, via the clearance 307 into the slot 306 and further through the tamping tube 505 to the inner seal 501 which is supported in the distal end of the pusher 506.

The tension of the filament 503 is provided by the pusher 506, the transverse portion in the proximal end 507 of the pusher being arrested in a seat 309 formed in a latch 310 that rises from the bottom 304 of slider 300, and the distal end of the pusher 506 being detachably connected to the inner seal 501 which is attached to the distal end of the filament 503. The length of the pusher 506 is determined with respect to the length of the filament 503 to provide a slight bias of the pusher 506, sufficient for tensioning the filament 503 as long as the proximal end of the pusher 506 is arrested by the latch 310, and the proximal end of the filament 503 is looped around the bar 308.

The seat 309 provides a snap lock connection with the pusher 506, by the latch 310 being depressible towards the bottom 304 of slider 300. Depression of the latch 310 causes the pusher 506 to be released from the seat 309 and free to slide in the slots 306, 306', towards the proximal end of the slider 300.

A heel 311, facing the proximal end of slider 300, is formed in the terminal end of an arm 312 rising from the bottom 304 of the slider 300. Similar to the latch 310, the arm 312 is depressible towards the bottom 304 of slider 300. However, for reasons that will be explained further on, the arm 312 is flexible and able to return to an operative position shown in the drawings. Advantageously, the latch 310 and the arm 312 are both flexible and formed integrally with the slider 300, made for example of a synthetic material such as a polymer material.

The latch 310 and the arm 312 are both formed with ramp surfaces 313, 314 interacting with a cam 210 which is stationary in the actuator 200. When assembled, the cam 210 reaches through the open top plane 303 to be received in the interior of slider 300 as will be further explained with reference to FIGS. 14a-e.

In the illustrated embodiment of FIGS. 14a-e, the actuator 200 is an elongate, hollow, four-sided body having an orthogonal section, dimensioned to receive the slider 300 for longitudinal movement therewith, and guiding the slider 300 for longitudinal displacement relative thereto. The actuator 200 is formed with opposed, vertical side walls 201, 202 connecting a horizontal top plane 203 with a horizontal bottom plane 204. Preferably, the longitudinal margins connecting the walls are chamfered in order to facilitate a sliding movement free from jamming in the sleeve 400.

Figure 14A:
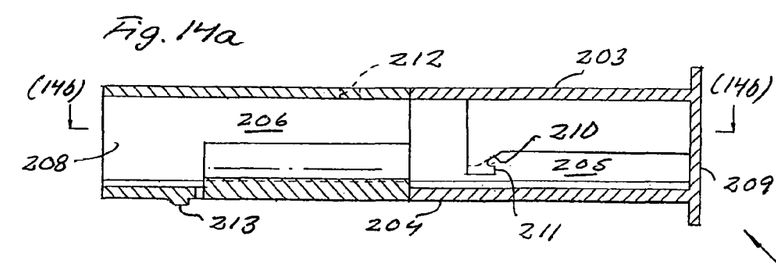
FIG. 14a is a longitudinal section, part of which is laterally displaced, through section (14a)-(14a) of FIG. 14b of an actuator incorporated in the closure device.
Figure 14B:
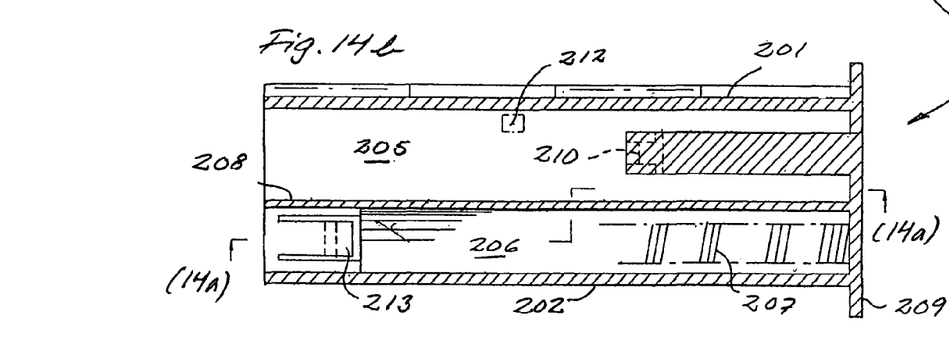
FIG. 14b is a sectional top view of the actuator of FIG. 14a through section (14b)-(14b)
Figure 14C:
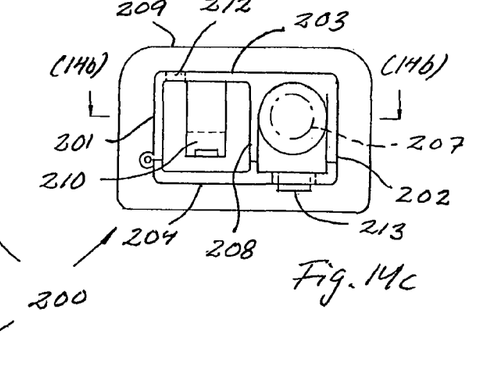
FIG. 14c is an elevation view showing the distal end of the actuator.

With reference to FIGS. 14a-14c, the actuator 200 is a two-piece element hinged together along one side thereof. A snap lock engagement may be formed on the opposite side for closing the actuator body. The interior of actuator 200 is divided into a first longitudinal chamber 205 formed to receive the slider 300, and a second longitudinal chamber 206 formed to receive a compressible spring 207 (shown diagrammatically through dash-dot lines in FIGS. 14b, 14c). Both chambers, separated by a longitudinal partition wall 208, open in the distal end of actuator 200. The proximal end thereof is closed, carrying a push-button 209.

Depending from the interior of top plane 203, a cam 210 reaches down into the chamber 205. In the assembled position, the cam 210 is received through the open top plane 303 of the slider 300 to a depth wherein the cam 210 is operative to engage and depress the ramp surfaces 313 and 314 in succession, i.e., first depressing the latch 310 and then the arm 312, when the slider 300 is displaced relative to the actuator 200.

Figure 14D:
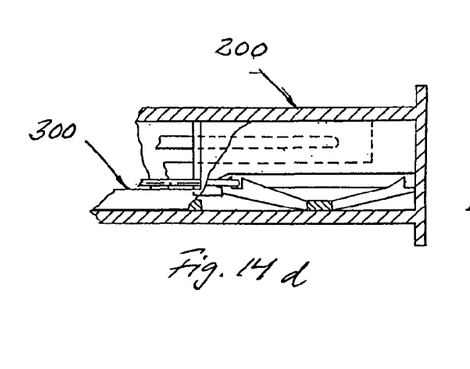
FIG. 14d is a partially broken away sectional view showing the slider and the actuator in a first relative position, realizing a first mode of operation.

In the first mode of operation for deployment of the inner seal 501, such as in FIGS. 7 and 14d, the proximal end of the slider 300 abuts the proximal push-button end of actuator 200, the actuator 200 thus pushing the slider 300 forward (towards the distal end) in a first relative position between slider and actuator.

Figure 14E:
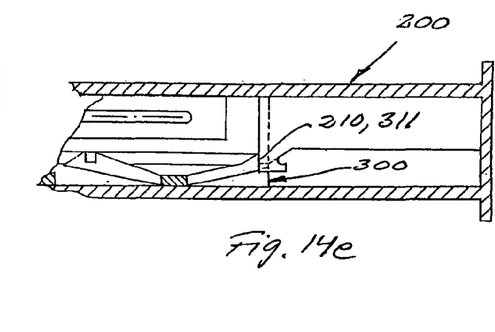
FIG. 14e is a partially broken away sectional view showing the slider and the actuator in a second relative position, realizing a second mode of operation.

In the second mode of operation for tamping the locking member 502, such as in FIGS. 9 and 14e, the cam 210 engages the heel 311 and the actuator 200 thus pushes the slider 200 in a second, advanced position relative to the actuator 200.

The displacement of the slider 300, from said first to said second position relative to the actuator 200, is caused by applying a pulling force upon retraction of the housing 100 in order to position the inner seal 501 over the puncture and in order to retract the distal end of the housing/insertion tube (see FIG. 8). During retraction, the slider 300 will remain stationary relative to the inner seal 501, connected therewith through the filament 503. A pulling force, applied to the actuator 200 via the housing 100 and the sleeve 400, and thus acting on/carried by the filament 503, causes ejection of the spring biased actuator 200, and brings the cam 210 to engage the ramp on latch 310 which is depressed by the moving cam to release the pusher 506 from the seat 309. Further motion of the actuator cam 210 will bring the pusher 506 along, the transverse portion 507 of the pusher being caught by a hook 211 that is formed on the cam 210. Next, the cam 210 engages the ramp 314 on arm 312, which is depressed to let the cam 210 pass to the proximal side of the heel 311. Due to the flexibility of arm 312, the arm returns to its original position wherein the heel 311 projects into the path of the cam 210, thus arresting the slider 300 in a second and advanced position relative to the actuator 200. Simultaneously, the proximal end of the pusher 506 leaves the guiding slots 306, 306' formed on the interior of the slider walls. As the pusher 506 is released from engagement with the seat 309 and pulled backwards by the cam-and-hook formation 210, 211, the distal end of the pusher 506 is concurrently disconnected from the inner seal 501. When the proximal end of the pusher 506 leaves the slots 306, 306' in the slider walls, the distal end of the pusher 506 is also fully retracted into the distal end of the tamping tube 505.

The relative displacement between the actuator 200 and the slider 300 is thus initiated by the pulling force acting on the filament 503, and is then driven by the compressible spring 207 as will be explained below.

Figures 15A, 15B, 15C:
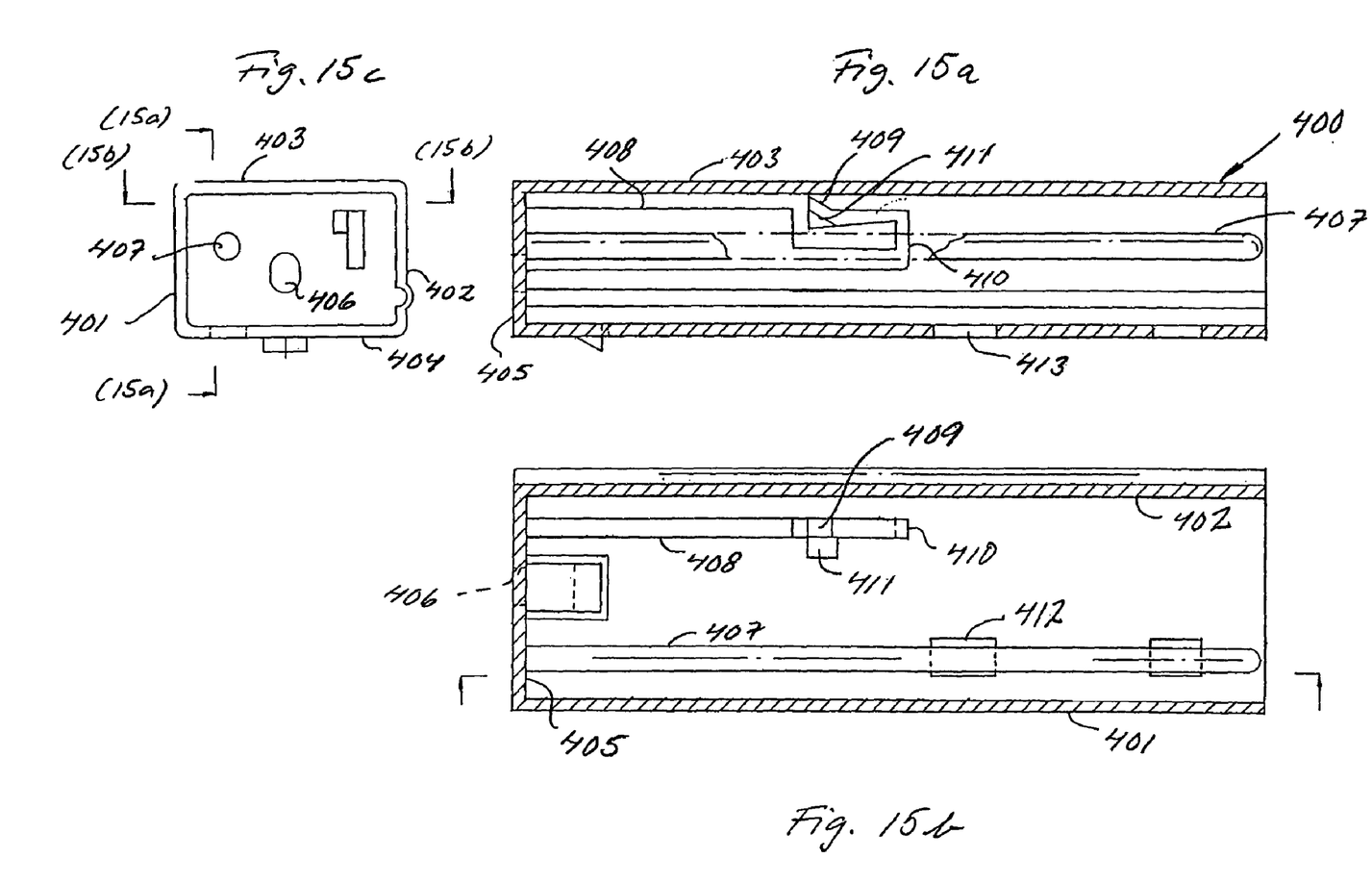
FIG. 15a is a longitudinal section through section (15a)-(15a) of FIG. 15c of a sleeve, incorporated in the closure device.
FIG. 15b is a sectional top view through section (15b)-(15b) of FIG. 15c of the sleeve.
FIG. 15c is an elevation view showing the proximal end of the sleeve.

With reference to FIGS. 15a-c, the sleeve 400 is an elongate, hollow, four-sided body having an orthogonal section, dimensioned to receive and guide the actuator 200 for longitudinal movement relative to the sleeve 400. The sleeve 400 is formed with opposed, vertical side walls 401, 402 connecting a horizontal top plane 403 with a horizontal bottom plane 404. Preferably, the longitudinal margins connecting the walls are chamfered in order to facilitate a jam free movement relative to the housing 100, accommodating the sleeve 400.

The sleeve 400 has an open proximal end receiving the actuator 200, and the distal end of the sleeve 400 being closed by an end wall 405. An opening 406 through the end wall 405 communicates with the passage through the forward portion 102 of the housing 100, guiding the seal assembly 500 into the insertion tube 101 of the closure device 1.

A rod 407 projects longitudinally through the sleeve 400, from the end wall 405 towards the proximal end. In the assembly, the rod 407 projects into the chamber 206 of the actuator 200 to support the spring 207, in this case a coiled spring 207, acting between the end wall 405 of the sleeve and the proximal or push-button end 209 of the actuator 200, and being compressed when the actuator 200 is depressed into the sleeve 400.

Also projecting from the end wall 405 is a beam 408, running in parallel with the rod 407 and aligned with the open interior of the slider 300 in the assembled position. The beam 408 runs with a clearance from the interior of top plane 403, substantially corresponding to a wall thickness in the top plane 203 of actuator 200. The beam 408 carries a latch 409 which is depressible towards the bottom plane 404 of the sleeve 400. The latch 409 is flexible to engage a slot 212 (see FIG. 14a), provided in the top plane 203 of the actuator 200 when the actuator is fully depressed into the sleeve 400 for deployment of the inner seal 501. The slot 212 and latch 409 provide a snap lock connection, the latch 409 being operative for retaining, temporarily as will be explained below, the actuator 200 with its distal end abutting the end wall 405 of the sleeve 400. In this end position of the actuator 200, which terminates the first mode of operation in a definite stop from where the actuator 200 is prevented from further movement in the distal direction, the proximal end 410 of the beam 408 is received in the distal end of the slider 300 which is engaged by the actuator 200 in said first relative position.

Reset of the actuator 200 will be described as follows. The latch 409 is associated with a ramp surface 411 which is laterally and vertically offset from the latch 409 and aligned to be operatively engaged by a cam 315, provided in the distal end of the slider 300 (see FIGS. 13a-d). Upon retraction of the insertion tool, the cam 315 on the slider 300 (which remains stationary) acts on the ramp surface 411 to depress the latch 409, which is then disengaged from the slot 212. The actuator 200 is thus disengaged from the snap lock connection 212, 409 to be ejected by action of the spring 207, the spring driving the actuator 200 in the proximal direction relative to the sleeve 400 and relative to the stationary slider 300.

The action of the spring 207 causes the release of the pusher 506, and resets the actuator 200 into a position from where the actuator 200 is operable and enabled for tamping the locking member 502. The spring actuated ejection of the actuator 200 is limited through a flexible latch 213, provided in a distal end portion of the actuator (FIG. 14c), snapping into engagement with a slot 412 provided on the sleeve 400. The latch 213 is formed with a ramp surface facing a distal margin of the slot 412, and a transverse surface engaging a proximal margin of the slot 412. From this arrested position the actuator 200 is operable to be depressed in the distal direction, but is however prevented from further movement in the proximal direction. Depression of the actuator 200 into the sleeve 400 will bring the slider 300 in the movement of the actuator 200, the cam 210 of the actuator engaging the heel 311 of the slider 300 in the second, advanced position relative to the actuator 200.

Release of the filament 503 will be described as follows. When the actuator 200 from this position is depressed into the sleeve 400 in the second mode of operation, the slider 300 is advanced in a forward or distal portion of the actuator 200. In this movement, the beam 408 which is stationary on the sleeve 400, moves longitudinally through the interior of the slider 300. The filament 503 which is looped around the bar 308 and crossing the interior of the slider 300, is then captured by the proximal end 410 of the beam 408 and caused thereby to slide towards the proximal end of the bar 308. Accordingly, the filament 503 remains stationary while the actuator 200, slider 300 and tamping tube 505 are advanced for slipping the locking member 502 into frictional engagement with the distal portion 504 of the filament 503. At the end of the tamping operation the filament loop has reached the proximal end of the bar 308, from where it is slipped off by action of the beam 408, the filament 503 thus being released from the slider 300. Obviously, all structures involved in the tamping operation are dimensioned with respect to structural lengths and lengths of movement to allow release of the filament 503 as the locking member has reached its final position on the filament 503, tamped against the outside of the vessel wall 3. Release of the filament 503 terminates the tamping operation, and the insertion tool can be removed from the patient.

The illustrated embodiment is one example of realization of the invention. Modifications to the detailed structure and design of components are possible without changing the basic solution, defined by the claims.

Instead of one integral actuator, e.g., a first actuator may be adapted for deployment of the inner seal 501 and a second actuator being adapted for tamping the locking member 502. In such case the slider 300 would be arranged to be disengaged from the first actuator and brought into engagement with the second actuator in response to a pulling force acting through the filament 503, while simultaneously the second actuator is set into an operable condition. Also, instead of being arranged about a common longitudinal axis as illustrated, the actuator 200, sleeve 400 and slider 300 may be of any conceivable shape as long as it is ensured that the first mode of operation terminates in a definite stop from where the tamping tube 505 and locking member 502 are prevented from further movement in the distal direction until the second mode of operation is enabled in response to a pulling force being applied to act on the filament 503.

A central feature of the new closure device 1 is, accordingly, that an actuator 200 in a first mode is operable for deployment of an inner seal 501, and is then reset into a second mode wherein the actuator 200 is operable for tamping a locking member 502. Reset of the actuator 200 is accomplished by applying a pulling force to act on the filament 503 that connects the inner seal 501 and the locking member 502. Thus, deployment of the inner seal 501, enabling of a second operable mode and tamping of the locking member 502 may all be performed in a one-hand operation. Also, an erroneous positioning of the locking member 502 inside the blood vessel is prevented by the actuator 200 preferably being disabled until a pulling force acting on the filament 503 causes the actuator 200 to be reset into an operable condition. A proper closure of the percutaneous puncture and ease of handling are thus both conceivably enhanced through a closure device as disclosed by the present invention.

What is claimed is:

1. A closure device for sealing a percutaneous puncture in the wall of a blood vessel, comprising:
    an inner member,
    an outer member,
    an insertion tool having a housing and an actuator which is operable in a first mode in which the actuator is configured to cause deployment of the inner member inside the vessel and operable in a second mode in which the actuator is configured to cause tamping of the outer member on an outside of the vessel,
    wherein the actuator is arranged to be set into said second mode in response to a pulling force acting on a filament connecting the inner member and the outer member, which causes an actuator portion to move relative to the housing so that the actuator is set into the second mode,
    wherein in the second mode, movement of the actuator portion relative to the housing causes said tamping of the outer member, and
    wherein the actuator portion is configured to be directly contacted by the user in both the first and second modes.

2. The closure device of claim 1, further comprising a seal assembly;
    wherein the housing is arranged to be positioned by a distal end of the housing for guidance of the seal assembly,
    the seal assembly comprising said inner member, attached to a distal end of said filament and said outer member, movably carried on the filament and spaced from the inner member;
    wherein the closure device further comprises:
        a pusher, guided in the housing, a distal end of the pusher detachably connected to the inner member;
        a tamping member, guided in the housing, the filament running through the tamping member and carrying the outer member and the inner member outside a distal end of the tamping member, and
        an actuator mechanism controlling the actuator in said first mode to drive the pusher for deployment of the inner member, whereupon the actuator mechanism is adapted to disable the actuator until the pulling force acting on the filament causes the actuator to be set into said second mode to drive the tamping member for tamping the outer member.

3. The closure device of claim 2, further comprising:
    a sleeve; and
    a slider;
    wherein the sleeve is telescopically received in the housing, the actuator is telescopically received in the sleeve, the seal assembly is operatively connected to the slider, and the slider is engaged by the actuator in a first relative position to be moved by the actuator for deployment of the inner member, and displaceable relative to the actuator into a second relative position wherein the slider is engaged by the actuator to be moved thereby for tamping the outer member.

4. The closure device of claim 3, wherein the slider is displaced from the first relative position to the second relative position in response to a pulling force being applied to the closure device and acting through the filament which is arrested by its distal end being attached to the inner member and by its proximal end being connected to the slider.

5. The closure device of claim 4, wherein the actuator is temporarily arrested in the sleeve and disabled in the second mode of operation, to be released by action of the slider as the slider is displaced from said first to said second relative position.

6. The closure device of claim 1, further comprising:
    a sleeve;
    a slider; and
    a seal assembly comprising said inner member and said outer member,
    wherein the sleeve is telescopically received in the housing, the actuator is telescopically received in the sleeve, the seal assembly is operatively connected to the slider, and the slider is engaged by the actuator in a first relative position to be moved by the actuator for deployment of the inner member, and displaceable relative to the actuator into a second relative position wherein the slider is engaged by the actuator to be moved thereby for tamping the outer member.

7. The closure device of claim 1, further comprising an actuator mechanism configured to control the actuator in said first mode, and configured to disable the actuator after deployment of the inner member until the pulling force acting on the filament causes the actuator to be set into said second mode.

8. The closure device of claim 1, further comprising a pusher, guided in the housing, a distal end of the pusher detachably connected to the inner member, wherein in said first mode, said pusher is engaged with said actuator, and wherein in said second mode, said pusher is disengaged from said actuator.

9. The closure device of claim 1, wherein said first and second modes are non-overlapping.

10. The closure device of claim 1, wherein the closure device is configured for one-hand operation from said first mode to said second mode.

11. The closure device of claim 1, wherein the actuator's position is automatically shifted when it is set in said second mode to provide an indication of the actuator being set in said second mode.

12. The closure device of claim 1, wherein the device comprises the outer member and wherein the outer member comprises a locking member.

13. The closure device of claim 1, wherein the device comprises the inner member and wherein the inner member comprises an inner seal.

14. The closure device of claim 1, wherein the actuator comprises a first actuator member for deployment of the inner member and a second actuator member for tamping the outer member.

15. The closure device of claim 1, further comprising a tamping member.

16. The closure device of claim 15, wherein the actuator is configured to be actuated in the second mode to tamp the outer member with the tamping member by contacting the outer member on an outside of the vessel with the tamping member.

17. A closure device for sealing a percutaneous puncture in the wall of a blood vessel, comprising:
  an inner member,
  an outer member,
  an insertion tool having a housing and an actuator which is operable in a first mode in which the actuator is configured to cause deployment of the inner member inside the vessel and operable in a second mode in which the actuator is configured to cause tamping of the outer member on an outside of the vessel,
  wherein the actuator is arranged to be set into said second mode in response to a pulling force acting on a filament connecting the inner member and the outer member,
  wherein the actuator is configured to be both contacted and operated by a user in both the first and second modes,
  wherein in the second mode, movement of the actuator relative to the housing causes said tamping of the outer member,
  a seal assembly;
  wherein the housing is arranged to be positioned by a distal end of the housing for guidance of the seal assembly,
  the seal assembly comprising said inner member, attached to a distal end of said filament and said outer member, movably carried on the filament and spaced from the inner member;
  wherein the closure device further comprises:
    a pusher, guided in the housing, a distal end of the pusher detachably connected to the inner member;
    a tamping member, guided in the housing, the filament running through the tamping member and carrying the outer member and the inner member outside a distal end of the tamping member, and
  an actuator mechanism controlling the actuator in said first mode to drive the pusher for deployment of the inner member, whereupon the actuator mechanism is adapted to disable the actuator until a pulling force acting on the filament causes the actuator to be set into said second mode to drive the tamping member for tamping the outer member;
  a sleeve;
  a slider;
  wherein the sleeve is telescopically received in the housing, the actuator is telescopically received in the sleeve, the seal assembly is operatively connected to the slider, and the slider is engaged by the actuator in a first relative position to be moved by the actuator for deployment of the inner member, and displaceable relative to the actuator into a second relative position wherein the slider is engaged by the actuator to be moved thereby for tamping the outer member;
  wherein the slider is displaced from the first relative position to the second relative position in response to a pulling force being applied to the closure device and acting through the filament which is arrested by its distal end being attached to the inner member and by its proximal end being connected to the slider;
  wherein the actuator is temporarily arrested in the sleeve and disabled in the second mode of operation, to be released by action of the slider as the slider is displaced from said first to said second relative position;
  a cam formed on a distal end of the slider and arranged to disengage a snap lock connection between the actuator and the sleeve; and a compressible spring, acting between the sleeve and the actuator, effective for ejecting the actuator into said second mode.

18. The closure device of claim 17, wherein the closure device is configured so that said pusher is released from the slider in response to the actuator being reset into said second mode.

19. The closure device of claim 18, further comprising a cam-and-hook formed on the actuator and arranged to disengage a snap lock connection between the slider and the pusher, and further to retract the pusher by the displacement of the slider relative to the actuator.

20. A closure device for sealing a percutaneous puncture in the wall of a blood vessel, comprising:
  an inner member,
  an outer member,
  an insertion tool having a housing and an actuator which is operable in a first mode in which the actuator is configured to cause deployment of the inner member inside the vessel and operable in a second mode in which the actuator is configured to cause tamping of the outer member on an outside of the vessel,
  wherein the actuator is arranged to be set into said second mode in response to a pulling force acting on a filament connecting the inner member and the outer member,
  wherein the actuator is configured to be both contacted and operated by a user in both the first and second modes, and
  wherein in the second mode, movement of the actuator relative to the housing causes said tamping of the outer member,
  a seal assembly;
  wherein the housing is arranged to be positioned by a distal end of the housing for guidance of the seal assembly,
  the seal assembly comprising said inner member, attached to a distal end of said filament and said outer member, movably carried on the filament and spaced from the inner member;
  wherein the closure device further comprises:
    a pusher, guided in the housing, a distal end of the pusher detachably connected to the inner member;
    a tamping member, guided in the housing, the filament running through the tamping member and carrying the outer member and the inner member outside a distal end of the tamping member, and
  an actuator mechanism controlling the actuator in said first mode to drive the pusher for deployment of the inner member, whereupon the actuator mechanism is adapted to disable the actuator until a pulling force acting on the filament causes the actuator to be set into said second mode to drive the tamping member for tamping the outer member;
  a sleeve;
  a slider;
  wherein the sleeve is telescopically received in the housing, the actuator is telescopically received in the sleeve, the seal assembly is operatively connected to the slider, and the slider is engaged by the actuator in a first relative position to be moved by the actuator for deployment of the inner member, and displaceable relative to the actuator into a second relative position wherein the slider is engaged by the actuator to be moved thereby for tamping the outer member;
  wherein the slider is displaced from the first relative position to the second relative position in response to a pulling force being applied to the closure device and acting through the filament which is arrested by its distal end being attached to the inner member and by its proximal end being connected to the slider;

wherein the actuator is temporarily arrested in the sleeve and disabled in the second mode of operation, to be released by action of the slider as the slider is displaced from said first to said second relative position;

wherein the proximal end of the filament is connected to the slider by a sliding connection having a bar, and captured by a beam formed on the sleeve so as to be released from the slider through relative movement of the beam as the slider moves with the actuator in said second mode.

21. The closure device of claim 1, wherein the distal end of the housing is associated with an insertion tube and a forward portion connected thereto, wherein said forward portion of the housing has separate passageways for a seal assembly and for a guiding member, respectively, said passageways converging into the insertion tube, and wherein said seal assembly comprises said inner member and said outer member.

22. The closure device of claim 21, wherein the housing, the forward portion, and the insertion tube are integrally formed.

23. A closure device for sealing a percutaneous puncture in the wall of a blood vessel, comprising:
   an inner member,
   an outer member,
   an insertion tool having a housing and an actuator which is operable in a first mode in which the actuator is configured to cause deployment of the inner member inside the vessel and operable in a second mode in which the actuator is configured to cause tamping of the outer member on an outside of the vessel,
   wherein the actuator is arranged to be set into said second mode in response to a pulling force acting on a filament connecting the inner member and the outer member, which causes an actuator portion to move relative to the housing so that the actuator is set into the second mode,
   wherein the housing supports the actuator in both the first and second modes,
   wherein the insertion tool comprises a mechanism configured such that, when the actuator is set in said second mode, a separate operation of the actuator causes movement of the outer member along the filament and towards the inner member and causes tamping of the outer member,
   wherein the actuator portion is configured to be directly contacted by a user in both the first and second modes.

24. The closure device of claim 23, wherein the insertion tool comprises the same parts in both the first and second modes.

25. The closure device of claim 23, wherein the actuator's position is automatically shifted when it is set in said second mode to provide an indication of the actuator being set in said second mode.

26. The closure device of claim 23, wherein the device comprises the outer member and wherein the outer member comprises a locking member.

27. The closure device of claim 23, wherein the device comprises the inner member and wherein the inner member comprises an inner seal.

28. The closure device of claim 23, wherein the actuator comprises a first actuator member for deployment of the inner member and a second actuator member for tamping the outer member.

29. The closure device of claim 23, further comprising a tamping member.

30. The closure device of claim 29, wherein the actuator is configured to be actuated in the second mode to tamp the outer member with the tamping member by contacting the outer member on an outside of the vessel with the tamping member.

* * * * *